(12) United States Patent
Osumi et al.

(10) Patent No.: US 9,585,636 B2
(45) Date of Patent: Mar. 7, 2017

(54) ULTRASONIC DIAGNOSTIC APPARATUS, MEDICAL IMAGE PROCESSING APPARATUS, AND MEDICAL IMAGE PROCESSING METHOD

(71) Applicant: TOSHIBA MEDICAL SYSTEMS CORPORATION, Otawara-Shi, Tochigi-Ken (JP)

(72) Inventors: Ryota Osumi, Nasushiobara (JP); Kenichi Ichioka, Nasushiobara (JP)

(73) Assignee: TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 577 days.

(21) Appl. No.: 13/715,488

(22) Filed: Dec. 14, 2012

(65) Prior Publication Data

US 2013/0165788 A1    Jun. 27, 2013

(30) Foreign Application Priority Data

Dec. 26, 2011 (JP) .................................. 2011-283970
Oct. 22, 2012 (JP) .................................. 2012-233151

(51) Int. Cl.
 *A61B 8/08* (2006.01)
 *A61B 8/00* (2006.01)
 (Continued)

(52) U.S. Cl.
 CPC .......... *A61B 8/5207* (2013.01); *A61B 8/4444* (2013.01); *A61B 8/5269* (2013.01);
 (Continued)

(58) Field of Classification Search
 None
 See application file for complete search history.

(56) References Cited

U.S. PATENT DOCUMENTS 6,246,783 B1    6/2001  Avinash
8,202,221 B2    6/2012  Osumi
(Continued)

FOREIGN PATENT DOCUMENTS

CN    1219715 A      6/1999
CN    101452574 A    6/2009
(Continued)

OTHER PUBLICATIONS

Chinese Office Action with its English translation for Chinese Patent Application No: 201210553218.0 mailed on Apr. 18, 2014.

*Primary Examiner* — Katherine Fernandez
*Assistant Examiner* — Michael Kellogg
(74) *Attorney, Agent, or Firm* — Kenichiro Yoshida

(57) ABSTRACT

According to one embodiment, a first calculation unit calculates a first feature amount concerning an edge direction in a specific region. A second calculation unit calculates a second feature amount concerning an edge intensity or a brightness value in the specific region. A storage unit stores filter characteristics. The each filter characteristic is associated with a first feature amounts range and a second feature amounts range which ultrasonic images suitable for the each filter characteristic may have. A selection unit selects a filter characteristic corresponding to both the calculated first feature amount and the calculated second feature amount. An image filter unit applies an image filter having the selected filter characteristic.

11 Claims, 14 Drawing Sheets

(51) Int. Cl.
  *G06T 5/00* (2006.01)
  *G06T 5/20* (2006.01)
  *A61B 8/14* (2006.01)

(52) U.S. Cl.
  CPC .............. *G06T 5/002* (2013.01); *G06T 5/20* (2013.01); *A61B 8/14* (2013.01); *A61B 8/463* (2013.01); *A61B 8/488* (2013.01); *G06T 2207/10132* (2013.01); *G06T 2207/20016* (2013.01); *G06T 2207/20064* (2013.01); *G06T 2207/30056* (2013.01); *G06T 2207/30101* (2013.01)

(56) References Cited

U.S. PATENT DOCUMENTS

| | | | |
|---|---|---|---|
| 2008/0077011 A1* | 3/2008 | Azuma et al. | 600/443 |
| 2009/0171208 A1* | 7/2009 | Osumi et al. | 600/443 |
| 2009/0177086 A1* | 7/2009 | Steen | A61B 8/0858 600/443 |
| 2010/0228129 A1* | 9/2010 | Osumi | A61B 8/14 600/443 |
| 2012/0078104 A1* | 3/2012 | Osumi | A61B 8/5215 600/443 |
| 2012/0108973 A1* | 5/2012 | Osumi | A61B 8/06 600/443 |

FOREIGN PATENT DOCUMENTS

| | | |
|---|---|---|
| CN | 101822547 A | 9/2010 |
| JP | 2009-153918 A | 7/2009 |
| WO | 2006/118100 A1 | 11/2006 |

* cited by examiner

B-mode image concerning abdomen and liver

| Diagnostic region/living tissue | Average brightness value | Average edge direction |
|---|---|---|
| Carotid artery (running direction) | | |
| 1 | 0.4946 | 0.7743 |
| 2 | 0.3769 | 0.8372 |
| 3 | 0.3935 | 0.8426 |
| Carotid artery (section) | 0.4988 | 0.5949 |
| Abdomen | 0.7157 | 0.3526 |
| MSK | 0.716 | 0.7894 |
| Heart | 0.3476 | 0.3619 |

FIG. 5

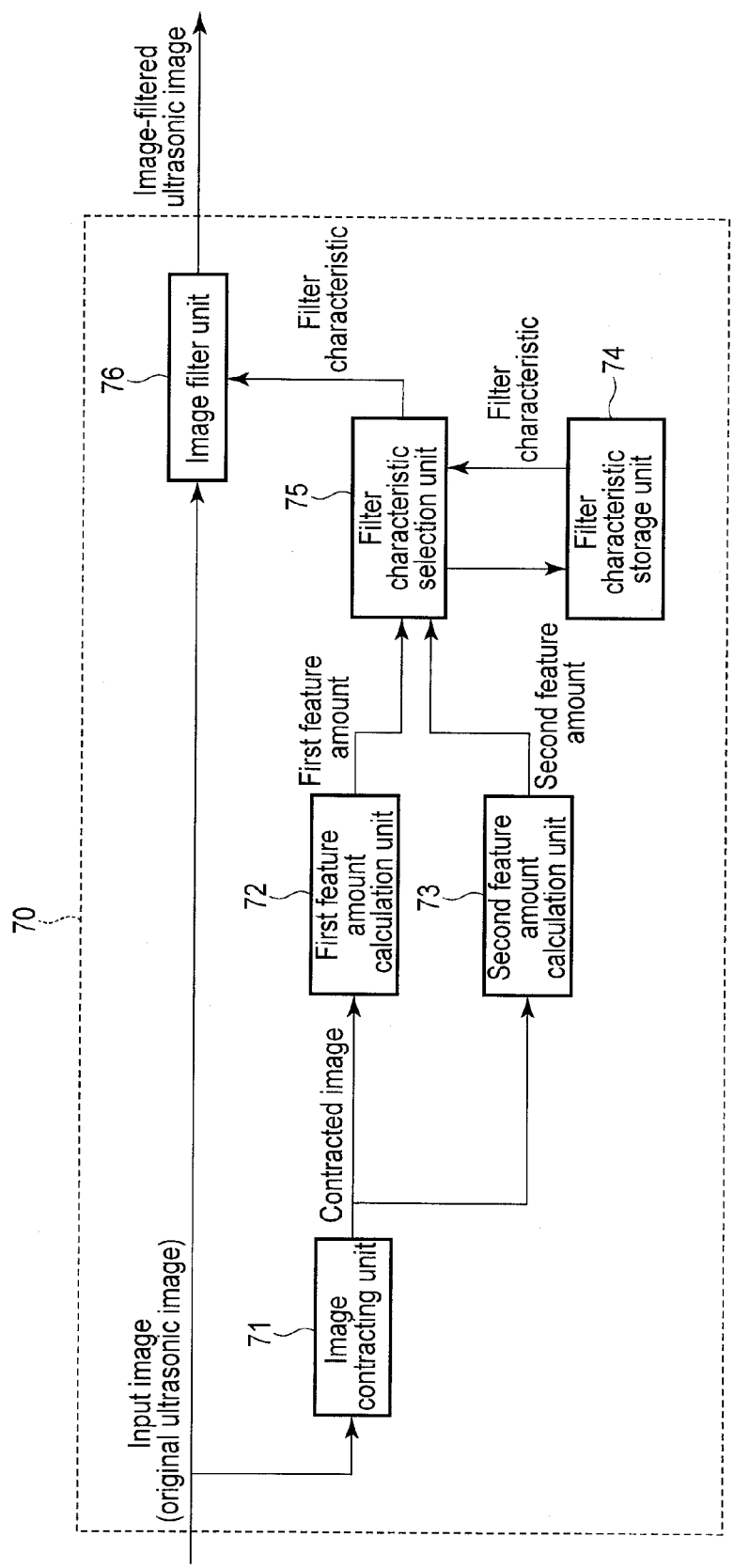
F I G. 6

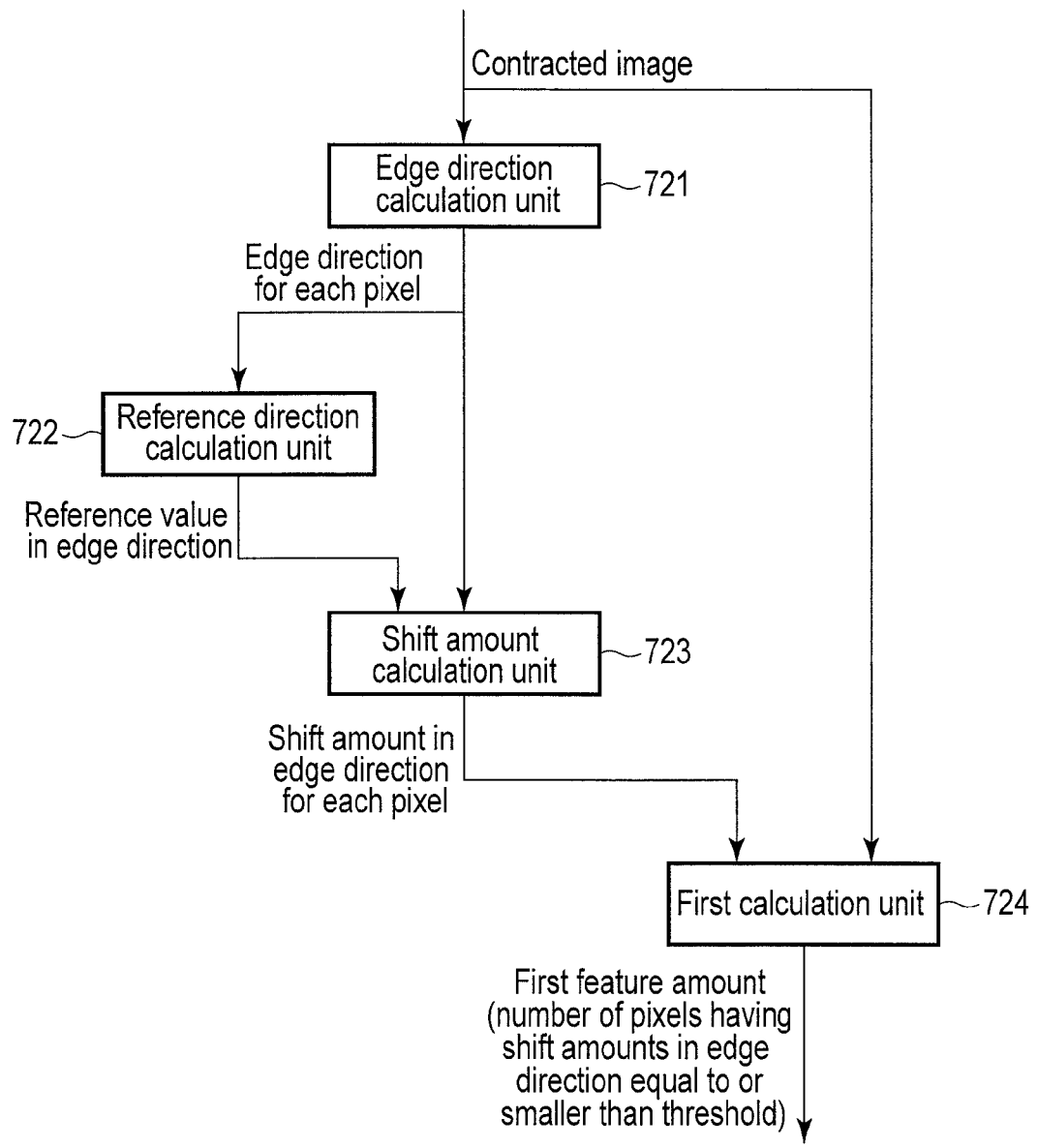
F I G. 11

| Parameter set | First feature amount (edge direction feature amount) | Second feature amount (brightness feature amount) |
|---|---|---|
| Parameter set 1 | Range 1-1 | Range 2-1 |
| Parameter set 2 | Range 1-2 | Range 2-2 |
| Parameter set 3 | Range 1-3 | Range 2-3 |
| ... | ... | ... |

F I G. 12

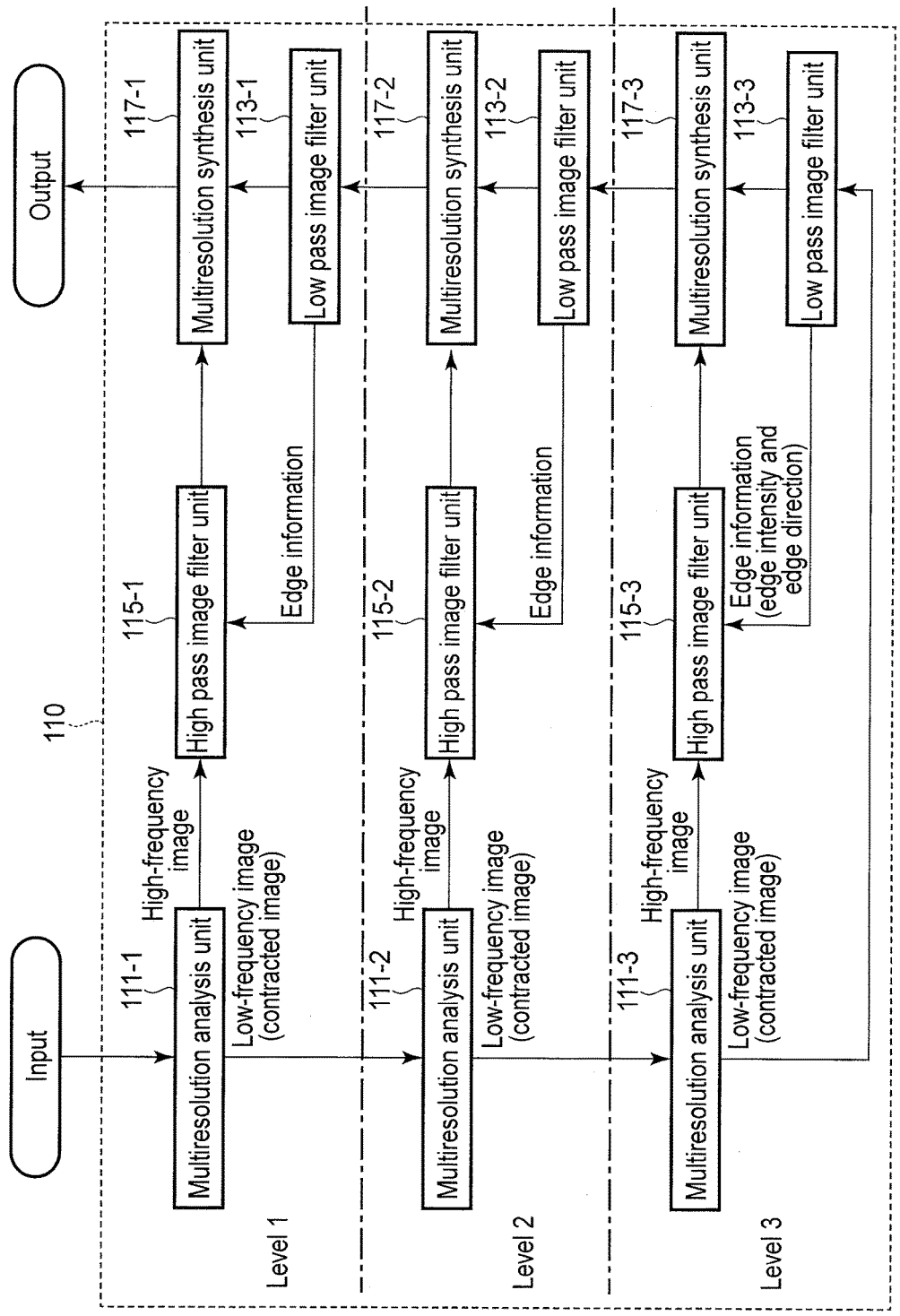
F I G. 13

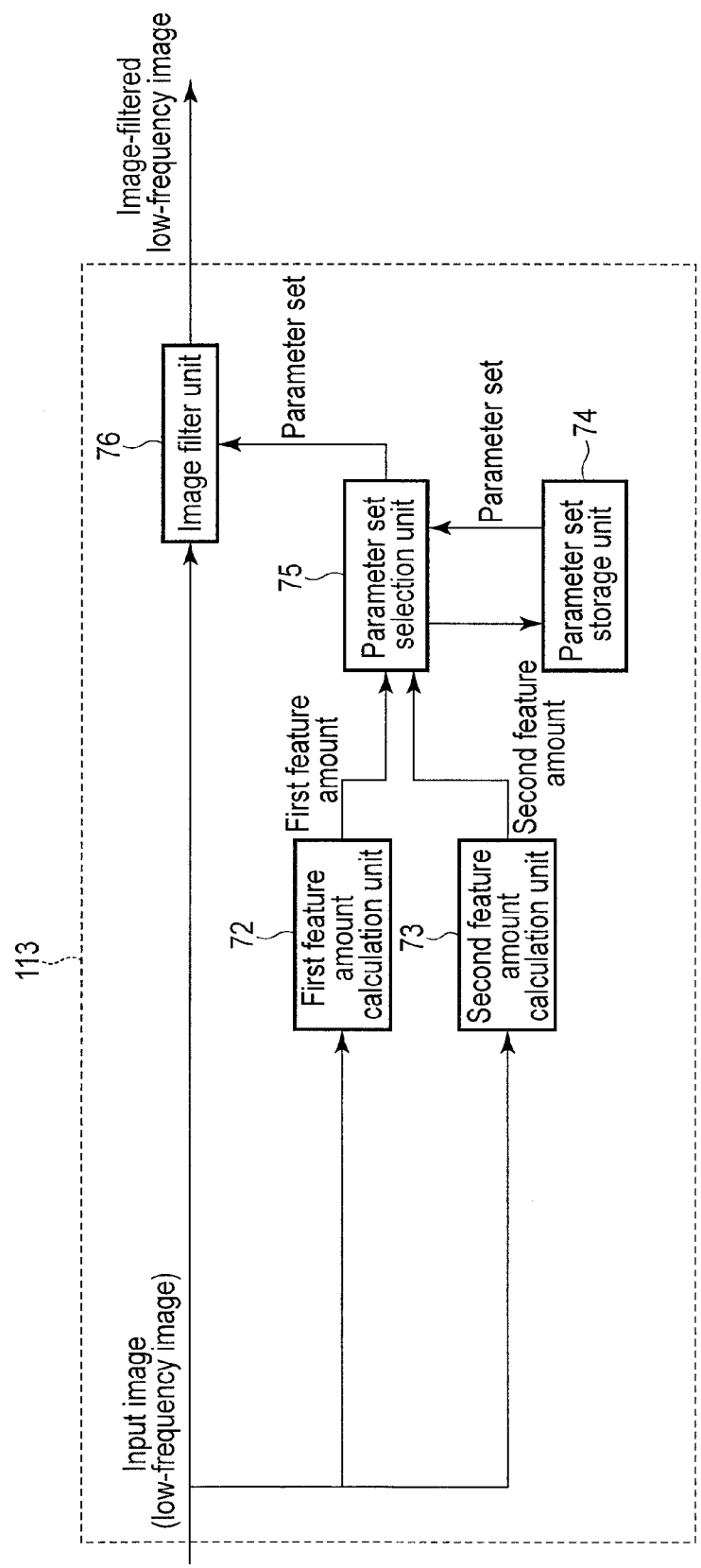
F I G. 14

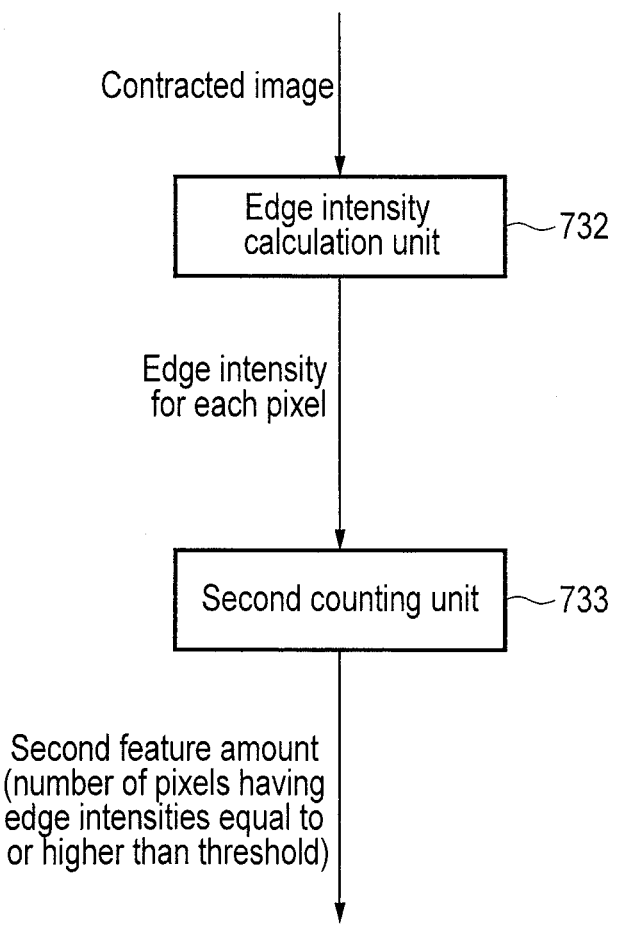
F I G. 15

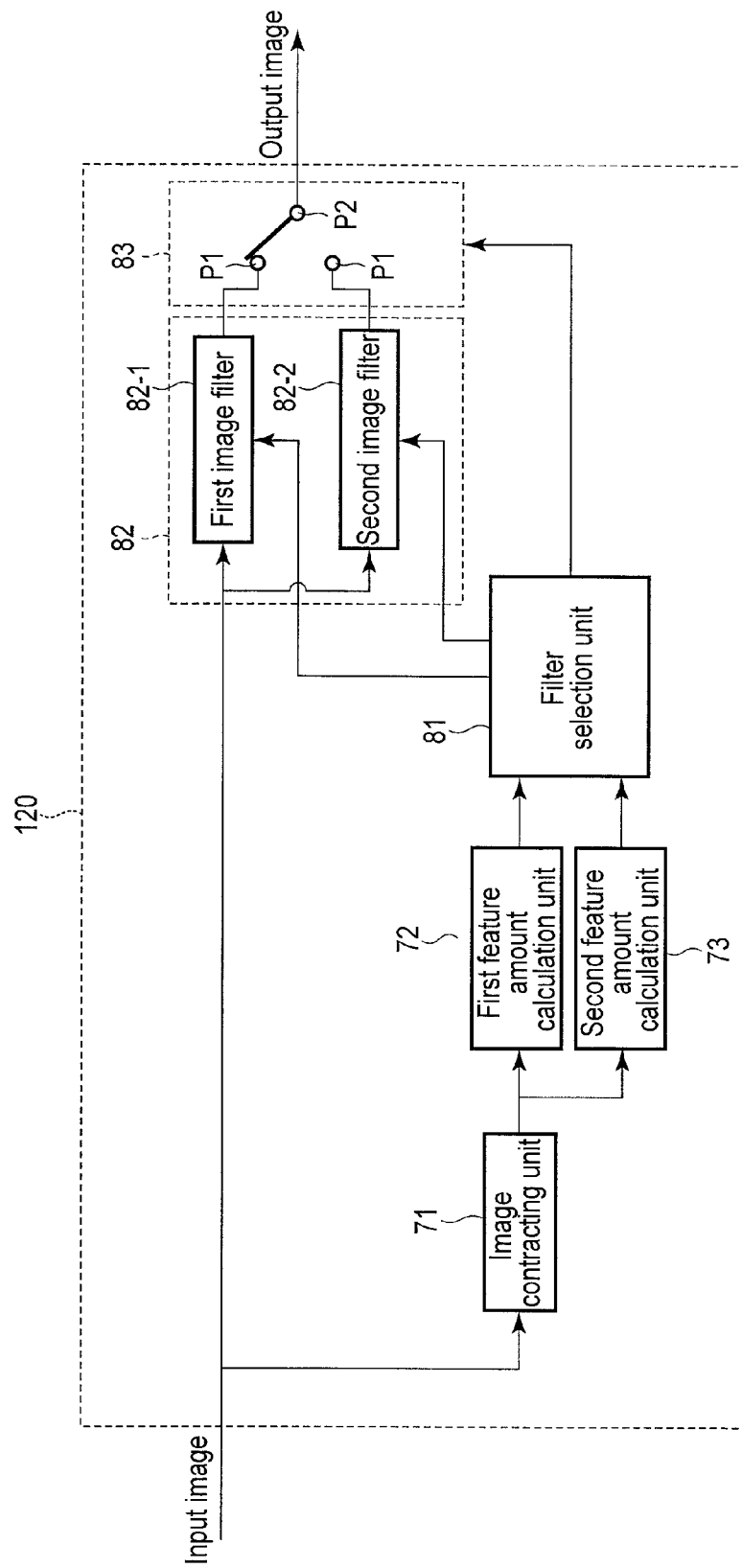
F I G. 16

ULTRASONIC DIAGNOSTIC APPARATUS, MEDICAL IMAGE PROCESSING APPARATUS, AND MEDICAL IMAGE PROCESSING METHOD

CROSS-REFERENCE TO RELATED APPLICATIONS

This application is based upon and claims the benefit of priority from Japanese Patent Applications No. 2011-283970, filed Dec. 26, 2011; and No. 2012-233151, filed Oct. 22, 2012, the entire contents of all of which are incorporated herein by reference.

FIELD

Embodiments described herein relate generally to an ultrasonic diagnostic apparatus, medical image processing apparatus, and medical image processing method.

BACKGROUND

An ultrasonic diagnostic apparatus transmits ultrasonic waves from an ultrasonic probe to a subject, receives the ultrasonic waves reflected by the subject via the ultrasonic probe, and generates an ultrasonic image based on an echo signal corresponding to the received ultrasonic waves. The ultrasonic image includes various kinds of noise and speckle due to ultrasonic interference other than information concerning the subject tissue. Noise and speckle degrade the image quality of the ultrasonic image.

There is available a method of reducing noise and speckle and enhancing information concerning a subject tissue by calculating the edge information of each pixel of an ultrasonic image and applying a filter corresponding to the calculated edge information to each pixel. More specifically, this filter smoothes the information in the edge direction and sharpens the information in a direction perpendicular to the edge direction. The image processing method using the filter is used to improve, for example, the image quality of a blood vessel image.

In this filtering method, it is preferable to optimize a filter characteristic in accordance with the behavior of a living tissue in a diagnostic region. In the present circumstances, a set of parameters for determining a filter characteristic is set in advance for each diagnostic region. In this case, the operator selects a parameter set corresponding to a diagnostic region as a scan target on an operation window, and a filter corresponding to the selected parameter set is applied to an ultrasonic image.

In ultrasonic examination, when the operator moves the ultrasonic probe, the diagnostic region or living tissue depicted in an ultrasonic image sometimes changes. Even if a selected parameter set is suitable for a diagnostic region or living tissue before movement, the parameter set is not always suitable for the diagnostic region or living tissue after the movement. If a parameter set is not suitable for a diagnostic region or living tissue, filtering suitable for the diagnostic region or living tissue is not performed, resulting in a deterioration in image diagnostic performance.

It is an object of an embodiment to provide an ultrasonic diagnostic apparatus, a medical image processing apparatus, and a medical image processing method which can improve image diagnostic performance.

BRIEF DESCRIPTION OF THE DRAWING

FIG. 5 is a view showing measurement results on an average brightness value and an average edge direction for each diagnostic region or living tissue, which are used in this embodiment;

FIG. 6 is a block diagram showing the arrangement of an image processing unit shown in FIG. 1;

FIG. 11 is a block diagram showing the arrangement of a first feature amount calculation unit shown in FIG. 6;

FIG. 12 is a view showing an example of a table associating the range of first feature amounts and the range of second feature amounts with each of parameter sets which are used in a filter characteristic storage unit in FIG. 6;

FIG. 13 is a block diagram showing the arrangement of an image processing unit according to Example 1 of this embodiment;

FIG. 14 is a block diagram showing the arrangement of a low pass image filter in FIG. 13;

FIG. 15 is a block diagram showing the arrangement of a second feature amount calculation unit according to a modification of this embodiment; and FIG. 16 is a block diagram showing the arrangement of an image processing unit according to Example 2 of this embodiment.

DETAILED DESCRIPTION

In general, according to one embodiment, an ultrasonic diagnostic apparatus includes an ultrasonic probe, image generation unit, first calculation unit, second calculation unit, storage unit, selection unit, and image filter unit. The ultrasonic probe transmits an ultrasonic wave to a subject, receive the ultrasonic wave reflected by the subject, and generate an echo signal corresponding to the received ultrasonic wave. The image generation unit generates an ultrasonic image concerning the subject based on the echo signal. The first calculation unit calculates a first feature amount concerning an edge direction in a specific region in the generated ultrasonic image. The specific region is larger than a kernel size of an image filter applied to the generated ultrasonic image. The second calculation unit calculates a second feature amount concerning an edge intensity distribution or a brightness value distribution in the specific region in the generated ultrasonic image. The storage unit stores filter characteristics. The each filter characteristic is associated with a range of first feature amounts and a range of second feature amounts which ultrasonic images suitable for the each filter characteristic are configured to have. The selection unit selects a filter characteristic corresponding to both the calculated first feature amount and the calculated second feature amount from the filter characteristics. The image filter unit applies an image filter having the selected filter characteristic to the generated ultrasonic image.

An ultrasonic diagnostic apparatus, medical image processing apparatus, and medical image processing method according to this embodiment will be described below with reference to the accompanying drawing.

Figure 1:
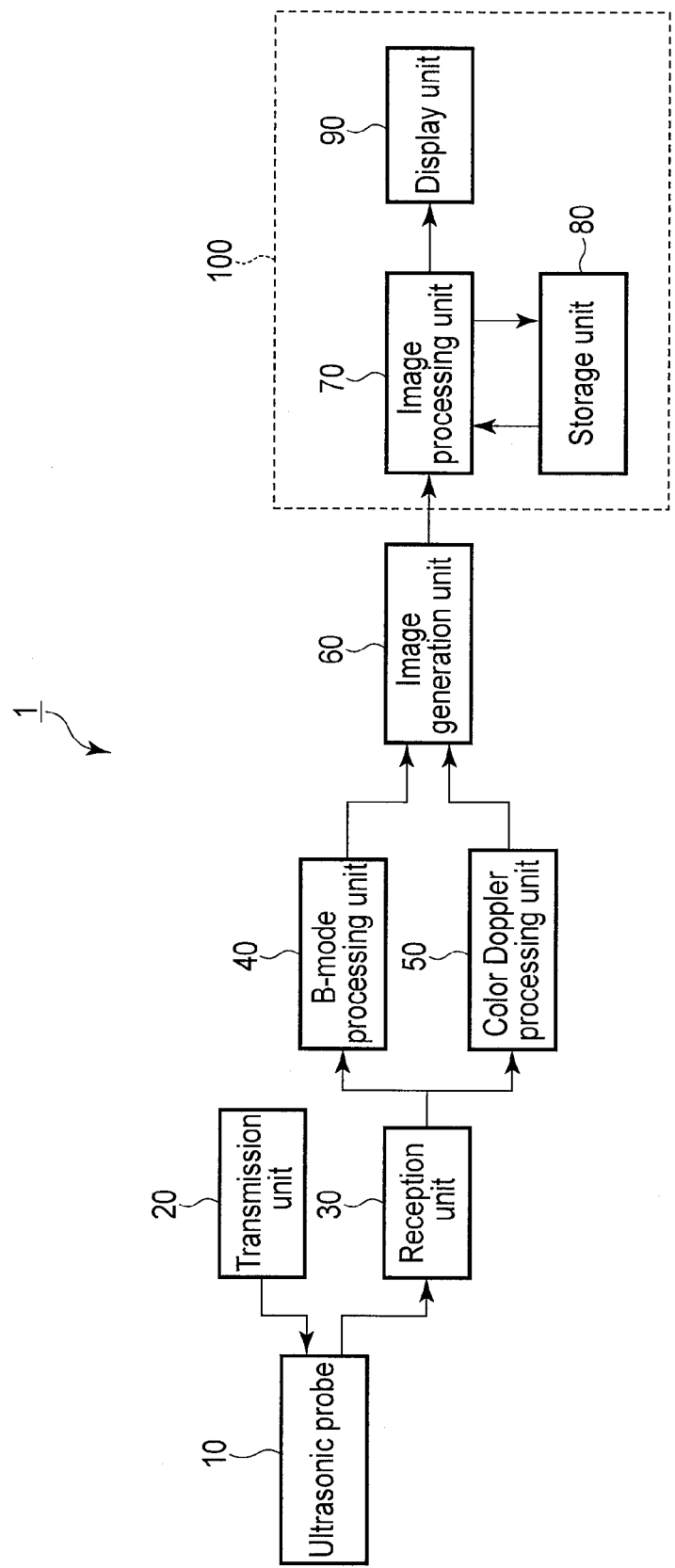
FIG. 1 is a block diagram showing the arrangement of an ultrasonic diagnostic apparatus according to this embodiment.

FIG. 1 is a block diagram showing the arrangement of an ultrasonic diagnostic apparatus 1 according to this embodiment. As shown in FIG. 1, the ultrasonic diagnostic apparatus 1 includes an ultrasonic probe 10, a transmission unit 20, a reception unit 30, a B-mode processing unit 40, a color Doppler processing unit 50, an image generation unit 60, an image processing unit 70, a storage unit 80, and a display unit 90.

The ultrasonic probe 10 includes transducers. Upon receiving a driving signal from the transmission unit 20, the ultrasonic probe 10 transmits ultrasonic waves to a subject. The ultrasonic waves transmitted to the subject are sequentially reflected by a discontinuity surface of acoustic impedance of living tissue in the subject. The ultrasonic probe 10 receives the reflected ultrasonic waves. The ultrasonic probe 10 generates an electrical signal (echo signal) corresponding to the intensity of the received ultrasonic waves. The amplitude of the echo signal depends on an acoustic impedance difference on the discontinuity surface by which the ultrasonic waves have been reflected. The frequency of the echo signal produced when ultrasonic waves are reflected by the surface of a moving subject such as a moving blood flow or the cardiac wall is subjected to a frequency shift depending on the velocity component of the moving body in the ultrasonic transmission direction due to the Doppler effect.

The transmission unit 20 repeatedly transmits ultrasonic waves to the subject via the ultrasonic probe 10. More specifically, the transmission unit 20 includes a rate pulse generating circuit, transmission delay circuit, and driving pulse generating circuit (none of which are shown) for the transmission of ultrasonic waves. The rate pulse generating circuit repeatedly generates rate pulses for each channel at a predetermined rate frequency fr Hz (period: 1/fr sec). The delay circuit gives each rate pulse the delay time required to focus an ultrasonic wave into a beam and determine transmission directivity for each channel. The driving pulse generating circuit applies a driving pulse to the ultrasonic probe 10 at the timing based on each delayed rate pulse.

The reception unit 30 repeatedly receives ultrasonic waves from the subject via the ultrasonic probe 10. More specifically, the reception unit 30 includes an amplifier circuit, A/D converter, reception delay circuit, and adder (none of which are shown) for the reception of ultrasonic waves. The amplifier circuit receives echo signals from the ultrasonic probe 10 and amplifies the received echo signals on a channel basis. The A/D converter converts the amplified echo signals from analog signals to digital signals on a channel basis. The reception delay circuit gives each echo signal converted into a digital signal the delay time required to focus the signal into a beam and determine reception directivity for each channel. The adder then adds the respective echo signals to which the delay times are given. This addition processing generates reception signals corresponding to the received beams. In this manner, the reception unit 30 generates reception signals respectively corresponding to reception beams. The reception signals are supplied to the B-mode processing unit 40 and the color Doppler processing unit 50.

The B-mode processing unit 40 logarithmically amplifies the reception signals from the reception unit 30 and detects the envelopes of the logarithmically amplified reception signals, thereby generating the data of B-mode signals representing the intensities of the echo signals with brightness. The data of the generated B-mode signals are supplied to the image generation unit 60.

The color Doppler processing unit 50 performs autocorrelation computation of a reception signal from the reception unit 30 to extract a blood flow, tissue, and contrast agent echo component by the Doppler effect, and generates the data of a Doppler signal expressing the intensity of blood flow information such as an average velocity, variance, and power in color. The generated data of the Doppler signal is supplied to the image generation unit 60.

The image generation unit 60 generates a B-mode image concerning a subject based on a B-mode signal from the B-mode processing unit 40. More specifically, the image generation unit 60 is formed from a scan converter. The image generation unit 60 generates a B-mode image by converting the scan scheme of a B-mode signal from the ultrasonic scan scheme to the display device scheme. Each pixel of the B-mode image has a brightness value corresponding to the intensity of a B-mode signal from which it originates. Likewise, the image generation unit 60 generates a Doppler image concerning the subject based on a Doppler signal from the color Doppler processing unit 50. Each pixel of the Doppler image has a color value corresponding to the intensity of a Doppler signal from which it originates. The B-mode image and the Doppler image are supplied to the image processing unit 70 and the storage unit 80.

The image processing unit 70 executes image processing for a B-mode image or Doppler image from the image generation unit 60 or the storage unit 80. More specifically, the image processing unit 70 applies, to the B-mode image or Doppler image, an image filter having a filter characteristic optimal for the living tissue depicted in the B-more image or Doppler image. Filter processing will generate a B-mode image or Doppler image with reduced speckle and noise. The image processing will be described in detail later. The B-mode image or Doppler image for which the image processing has been performed is supplied to the storage unit 80 and the display unit 90.

The display unit 90 displays the B-mode image processed by the image processing unit 70 on the display device. In this case, the Doppler image may be superimposed on the B-mode image. As the display unit, for example, a CRT display, liquid crystal display, organic EL display, plasma display, or the like can be used as needed.

Note that the image processing unit 70, the storage unit 80, and the display unit 90 constitute a medical image processing apparatus 100. As shown in FIG. 1, the medical image processing apparatus 100 may be incorporated in the ultrasonic diagnostic apparatus 1 or a computer separate from the ultrasonic diagnostic apparatus 1. If the medical image processing apparatus 100 is separate from the ultrasonic diagnostic apparatus 1, the medical images to be processed by the medical image processing apparatus 100 are not limited to the images generated by the ultrasonic diagnostic apparatus 1. For example, the medical image processing apparatus 100 may be designed to process the X-ray images generated by an X-ray diagnostic apparatus, the CT images generated by an X-ray computed tomography apparatus, the MR images generated by a magnetic resonance imaging apparatus, the SPECT images generated by a SPECT apparatus, or the PET images generated by a PET apparatus. For the sake of a concrete description, assume that the medical images in the following description are ultrasonic images.

The image processing unit 70 according to this embodiment will be described in detail below.

The characteristics of a B-mode image concerning each diagnostic region or living tissue will be described first. Assume that in this embodiment, a diagnostic region indicates a body region with which the ultrasonic probe comes into contact, e.g., the head region, chest region, or abdomen, and a living tissue indicates a tissue such as the blood vessel, muscle fiber (MSK: musculoskeletal), liver, or heart.

Figure 2:
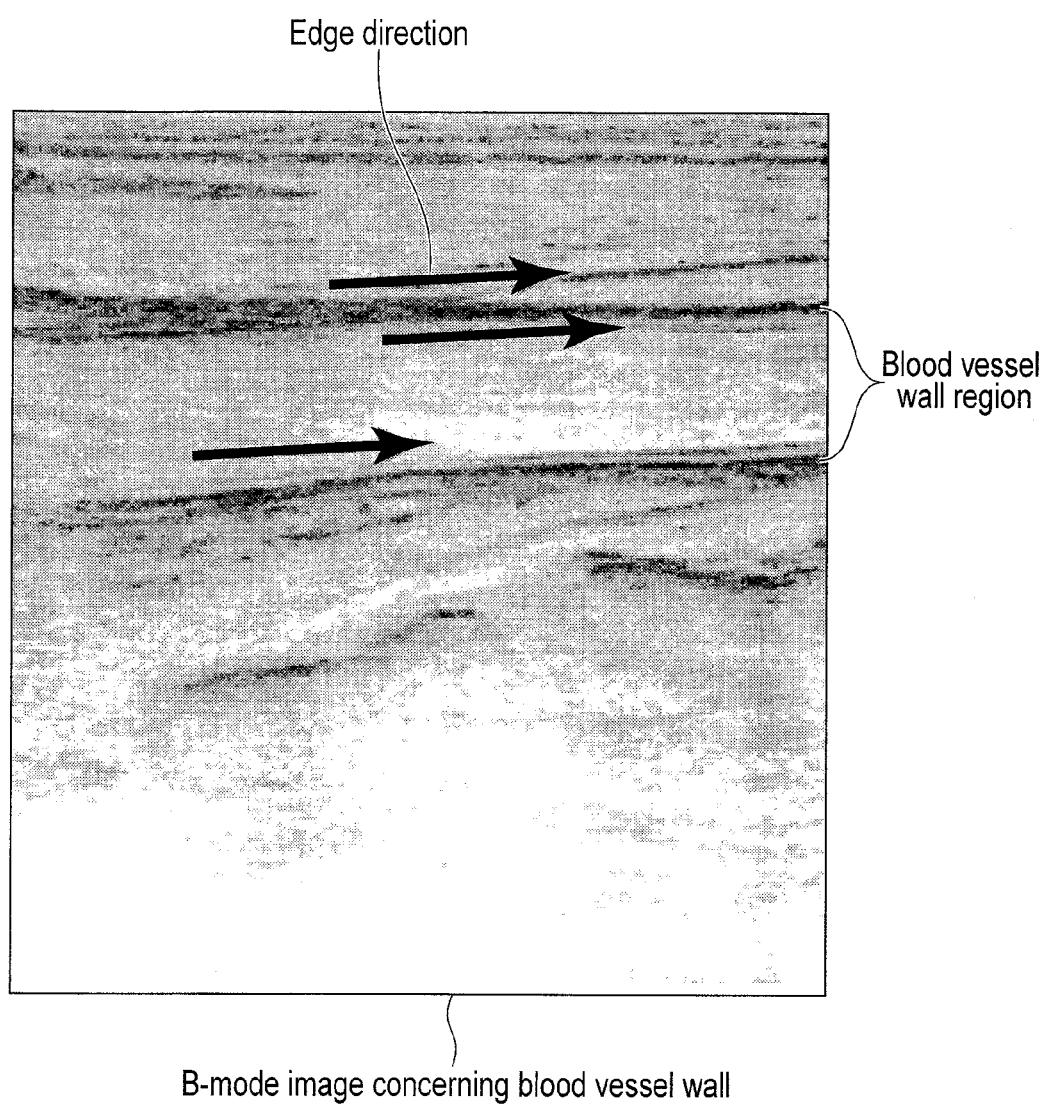
FIG. 2 is a view showing an example of a B-mode image concerning the blood vessel wall.
Figure 3:
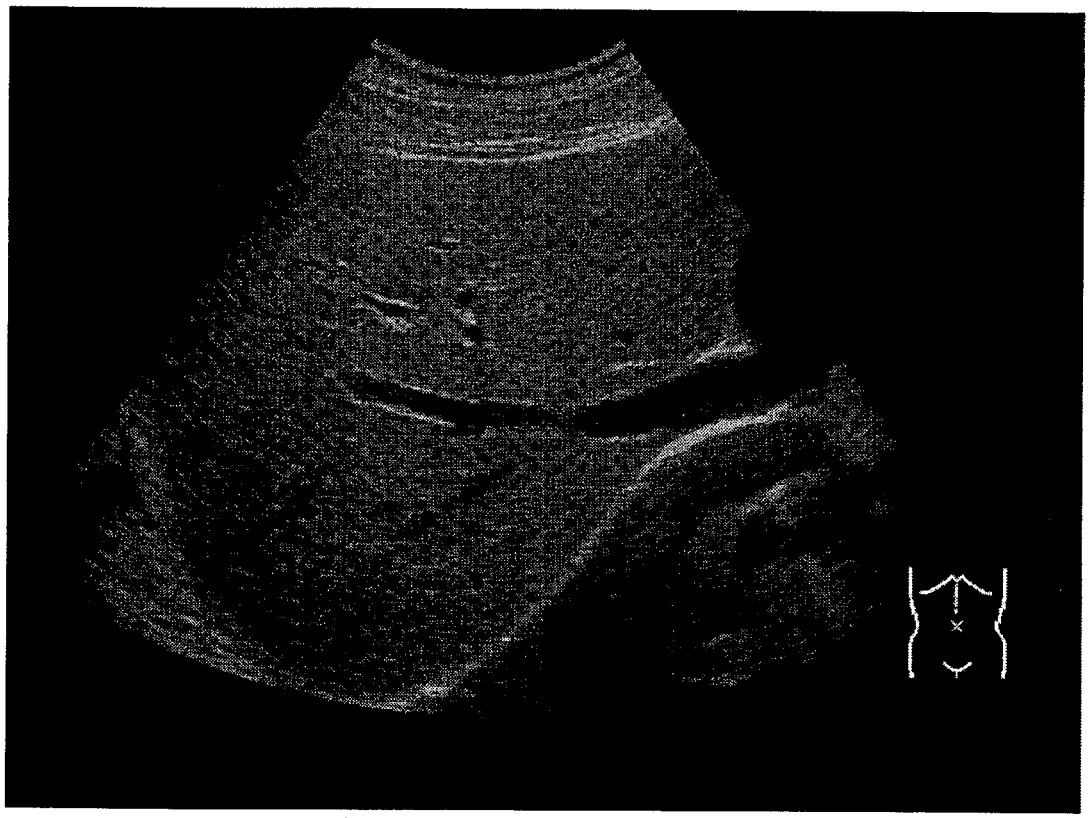
FIG. 3 is a view showing an example of a B-mode image concerning the abdomen and the liver.
Figure 4:
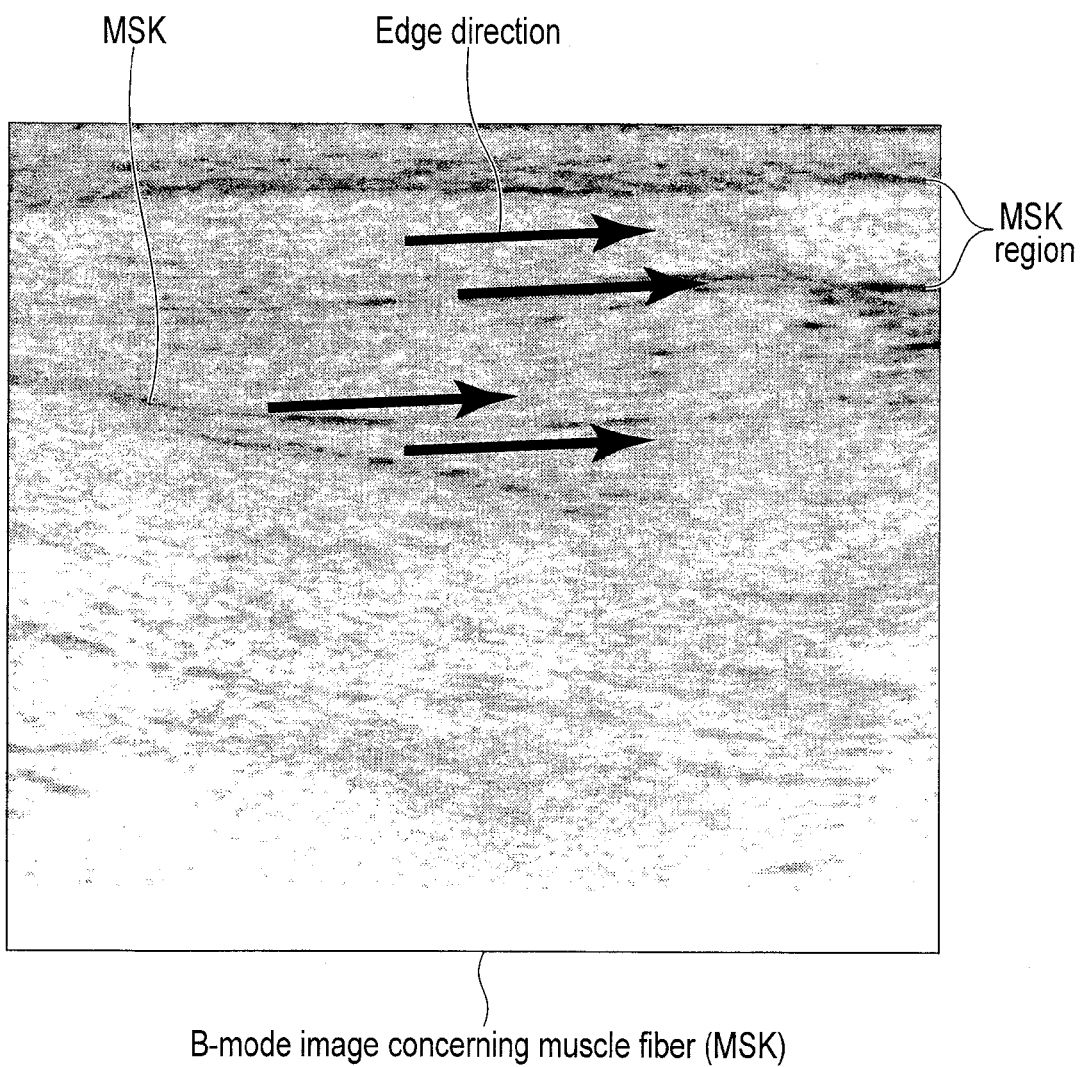
FIG. 4 is a view showing an example of a B-mode image concerning a muscle fiber (MSK: musculoskeletal)

FIG. 2 is a view showing an example of a B-mode image concerning the blood vessel wall. FIG. 3 is a view showing an example of a B-mode image concerning the abdomen and the liver. FIG. 4 is a view showing an example of a B-mode image concerning the muscle fiber (MSK). As shown in FIG. 2, a B-mode image concerning the blood vessel wall includes a pixel region (blood vessel wall region) concerning the blood vessel wall. A B-mode image concerning the blood vessel wall globally includes edges extending along a specific direction in a blood vessel wall region. In the case shown in FIG. 2, edges run laterally on the drawing surface. A B-mode image concerning the blood vessel wall includes regions having low brightness values at specific depths (the regions indicated in black in FIG. 2) as compared with B-mode images concerning other regions and living tissues. As shown in FIG. 3, a B-mode image concerning the abdomen and the liver does not globally have any edges extending along a specific direction. In addition, the B-mode image concerning the abdomen and the liver includes regions having high brightness values (the regions indicated in white in FIG. 3) which are distributed in a wide range as compared with B-mode images concerning other regions and living tissues. As shown in FIG. 4, a B-mode image concerning MSK includes a pixel region (MSK region) concerning MSK. In the B-mode image concerning MSK, the MSK region globally includes edges extending along a specific direction. In the case of FIG. 4, the edges run in the lateral direction on the drawing surface. In addition, the B-mode image concerning MSK has regions having low brightness values (the regions indicated in black in FIG. 4) widely distributed as compared with B-mode images concerning other regions and living tissues.

FIG. 5 is a view showing measurement results on an average brightness value and an average edge direction for each diagnostic region or living tissue. Referring to FIG. 5, the diagnostic regions and the living tissues include the carotid artery, abdomen, muscle fiber (MSK), and heart. Note that the carotid artery (running direction) indicates a B-mode image concerning the carotid artery, whose section is parallel to the center line of the carotid artery. The carotid artery (section) is a B-mode image concerning the carotid artery, and its section is perpendicular to the center line of the carotid artery. An average brightness value is the average value of the brightness values of pixels included in the B-mode image. The average edge direction is an average value in the edge direction of pixels included in the B-mode image. Although the edge direction will be described in detail later, the higher the average edge direction, the more the edge directions of the respective pixels are aligned in a specific direction.

As shown in FIG. 5, in the B-mode image concerning the carotid artery (running direction), the average brightness value is statistically low, and the average edge direction is statistically high as compared with those in B-mode images concerning other diagnostic regions and living tissues. In the B-mode image concerning the abdomen, the average brightness value is statistically high, and the average direction is statistically low as compared with those in B-mode images of other diagnostic regions and living tissues. In the B-mode image concerning the muscle fiber, the average brightness value is statistically high, and the average direction is statistically high as compared with those in B-mode images of other diagnostic regions and living tissues. In the B-mode image concerning the heart, the average brightness value is statistically low, and the average direction is statistically low as compared with those in B-mode images of other diagnostic regions and living tissues.

For example, living tissues globally having edge directions in a specific direction include the blood vessel and MSK. It is therefore impossible to discriminate a B-mode image concerning the blood vessel from a B-mode image concerning MSK according to only edge directions. The B-mode image concerning the blood vessel includes relatively many low-brightness regions, whereas the B-mode image concerning MSK includes relatively few low-brightness regions. As described above, a B-mode image have a unique edge direction and brightness value distribution for each diagnostic region or living tissue.

By using a unique edge direction and brightness value distribution for each diagnostic region and living tissue, the image processing unit 70 selects a filter characteristic that produces a filtering effect optimal for a B-mode image in accordance with the global edge direction and brightness value distribution of the B-mode image, and applies an image filter having the selected filter characteristics to the B-mode image.

The image processing unit 70 will be described in detail below. Note that the image processing unit 70 may process either a B-mode image or a Doppler image. For the sake of descriptive convenience, B-mode images and Doppler images will be collectively referred to as ultrasonic images.

FIG. 6 is a block diagram showing the arrangement of the image processing unit 70. As shown in FIG. 6, the image processing unit 70 receives an original ultrasonic image from the image generation unit 60 or the storage unit 80. The original ultrasonic image input to be filtered by the image processing unit 70 will be referred to as an input image hereinafter.

The image processing unit 70 will be described in detail below. A calculation target for the first and second feature amounts in the image processing unit 70 is limited to a specific region in an ultrasonic image. In this case, this specific region will be referred to as a calculation target region.

Figure 7:
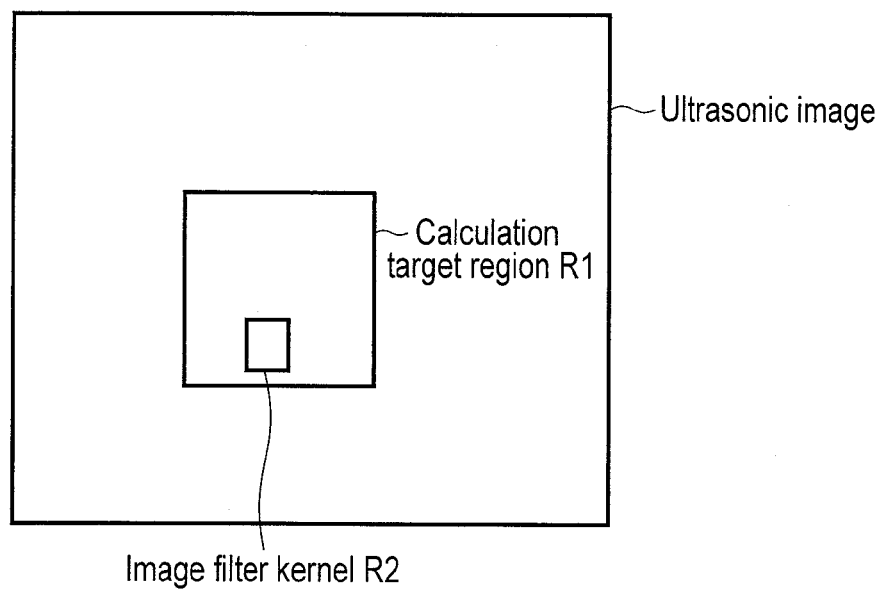
FIG. 7 is a view showing an example of a calculation target region in an ultrasonic image according to this embodiment.

FIG. 7 is a view showing an example of a calculation target region. As shown in FIG. 7, a calculation target region R1 is set in an ultrasonic image. The calculation target region R1 has a matrix size larger than the size (kernel size) of a kernel R2 of the image filter applied by an image filter unit 76 (to be described later). The calculation target region R1 may have the same matrix size as that of an ultrasonic image or a matrix size smaller than that of the ultrasonic image.

Figure 8:
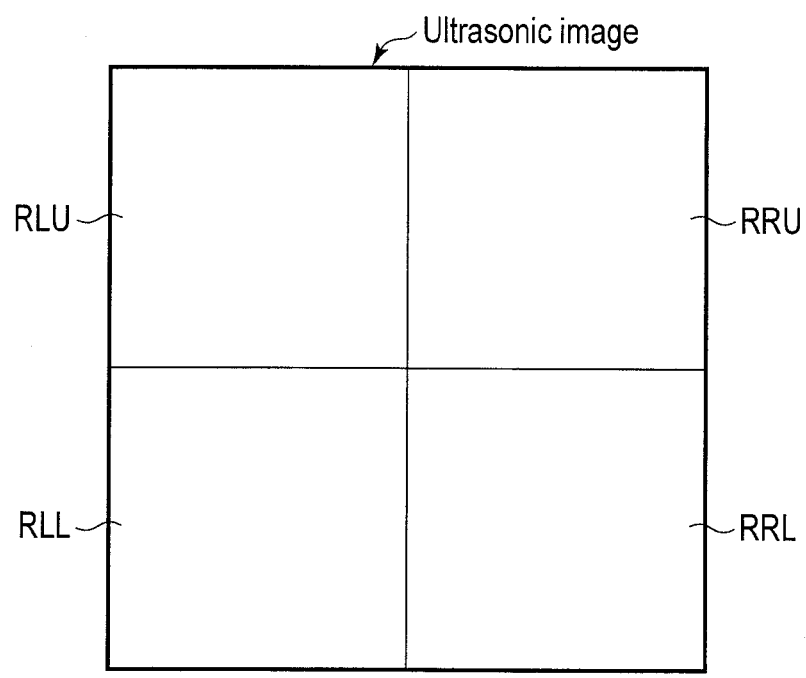
FIG. 8 is a view showing another example of the calculation target region according to this embodiment.
Figure 9:
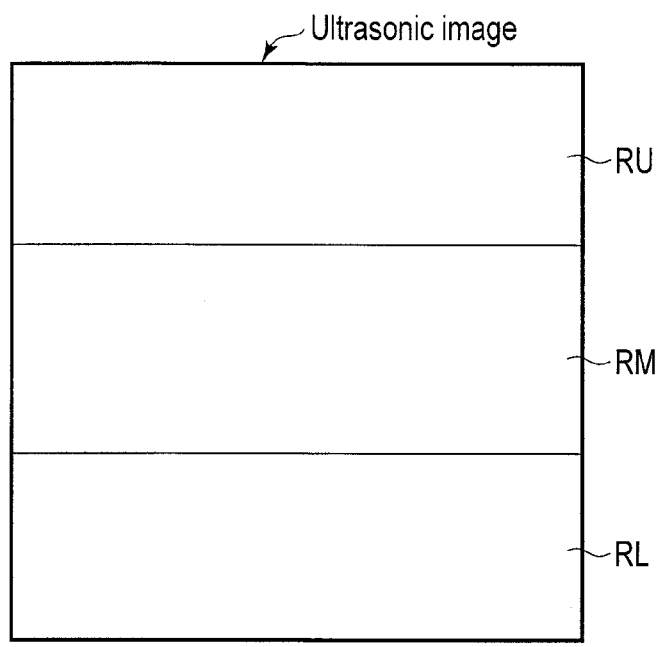
FIG. 9 is a view showing still another example of the calculation target region according to this embodiment.
Figure 10:
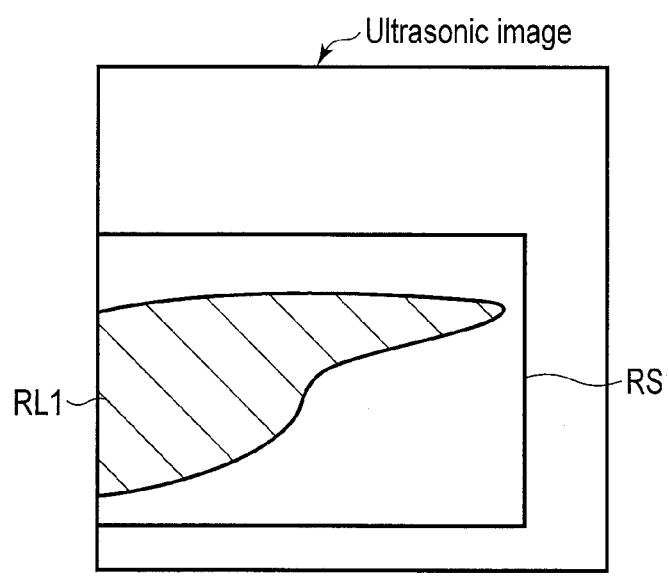
FIG. 10 is a view showing still another example of the calculation target region according to this embodiment.

A calculation target region is set by the user via an input device (not shown) or automatically set. The number of calculation target regions to be set may be one or more. For example, it is preferable to segment an ultrasonic image into regions and set each segmented region in a calculation target region. The arrangement of segmented regions is not specifically limited. For example, as shown in FIG. 8, an ultrasonic image may be segmented into an upper left region RLU, an upper right region RRU, a lower left region RLL, and a lower right region RRL. Alternatively, as shown in FIG. 9, an ultrasonic image may be segmented in accordance with a depth direction. In this case, an ultrasonic image may be segmented into a region RU located at the upper level in the depth direction, a region RM located at the intermediate level, and a region RL located at the lower level. In addition, as shown in FIG. 10, a calculation target region may be set so as to include a specific anatomical region included in an ultrasonic image. Assume that an ultrasonic image includes a pixel region RLI concerning the liver. As a technique for an anatomical region, for example, segmentation processing is known, which segments an anatomical region in an ultrasonic image according to geometrical characteristics, brightness value characteristics, or the like. Assume that an ultrasonic image includes the pixel region RLI concerning the liver. Segmentation processing extracts the liver region RLI from the ultrasonic image. A calculation target region RS is automatically set in a region including the liver region RLI. Note that the shape of a calculation target region is not limited to a rectangle and may be any shape such as a circle, a hexagon, or an arbitrary shape.

As shown in FIG. 6, the image processing unit 70 includes an image contracting unit 71, a first feature amount calculation unit 72, a second feature amount calculation unit 73, a filter characteristic storage unit 74, a filter characteristic selection unit 75, and the image filter unit 76.

The image contracting unit 71 generates an ultrasonic image having a matrix size smaller than that of an input image. The image generated by the image contracting unit 71 is referred to as a contracted image hereinafter. As image contraction processing, it is possible to use any existing image contraction technique such as resampling, pixel thinning-out operation, or multi-resolution analysis. Image contraction processing is performed to process an ultrasonic image with a proper resolution so as to globally grasp the feature amount of the ultrasonic image which is calculated by the first feature amount calculation unit 72 and the second feature amount calculation unit 73. In addition, performing image contraction processing will contract the matrix size of an ultrasonic image, and hence will improve the processing speed on the subsequent stage of the image contracting unit 71. Image contraction processing contracts a calculation target region at almost the same contraction ratio as that of an ultrasonic image.

The first feature amount calculation unit 72 calculates the first feature amount (to be referred to as an edge direction feature amount hereinafter) concerning the edge direction in the calculation target region in the ultrasonic image. The edge direction in the calculation target region indicates the tendency of an edge direction in the anatomical region depicted in the calculation target region. In the following description, an edge direction in a calculation target region indicates a global edge direction.

FIG. 11 is a block diagram showing the arrangement of the first feature amount calculation unit 72. The first feature amount calculation unit 72 receives a contracted image from the image contracting unit 71. As shown in FIG. 11, the first feature amount calculation unit 72 includes an edge direction calculation unit 721, a reference direction calculation unit 722, a shift amount calculation unit 723, and a first calculation unit 724.

The edge direction calculation unit 721 calculates the edge direction of each of the pixels included in a calculation target region in a contracted image based on the spatial differentiation of the brightness value of each pixel. More specifically, first of all, the edge direction calculation unit 721 calculates a spatial derivative by performing spatial differentiation along the respective coordinate axes (specifically, the x- and y-axes) of the ultrasonic image by using a processing target pixel and neighboring pixels of the processing target pixel. The edge direction calculation unit 721 then calculates an edge direction concerning the processing target pixel based on the calculated spatial derivative. More specifically, the edge direction calculation unit 721 calculates elements of the structure tensor of the processing target pixel by using the spatial derivative. The edge direction calculation unit 721 applies linear algebraic computation to the calculated elements to calculate the two eigenvalues and two eigenvectors of the structure tensor. One of the two eigenvectors indicates a direction along an edge, and the other eigenvector indicates a direction perpendicular to the edge. In this case, a direction along an edge will be referred to as an edge direction. Note that the eigenvalues of the structure tensor depend on the intensity of the edge. Note that the edge direction calculation method to be used is not limited to the method using a structure tensor. If it is possible to calculate a local edge direction, an edge direction may be calculated by using other methods such as Gabor transformation.

The reference direction calculation unit 722 calculates a reference direction concerning edge directions based on edge directions of pixels calculated by the edge direction calculation unit 721. The reference direction is set to the statistical value of edge directions. More specifically, it is preferable to set the reference direction to any one of the average value, maximum value, minimum value, intermediate value, and mode value of edge directions.

An edge direction is defined by an angle as a cyclic variable. If, therefore, an angle range is improperly set, simple computation of the average of edge directions or the like will calculate a reference direction with an improper value. Consider, for example, two angles $\theta_1$ and $\theta_2$ given by $\theta_1 = \pi - \delta\theta$ and $\theta_2 = \pi + \delta\theta$. Note that $|\delta\theta| \ll \pi$. The preferable average value of the angles $\theta_1$ and $\theta_2$ is $\pi$. If, however, the angle range is set to $-\pi < \theta < \pi$, aliasing treated as $\theta_2 = -\pi + \delta\theta$ occurs. As a result, the average becomes 0.

The reference direction calculation unit 722 therefore properly calculates a reference direction without any angle aliasing by the following two countermeasures.

(First Countermeasure): In the first countermeasure, the reference direction calculation unit 722 uses the phenomenon that an edge direction spatially continuously changes. More specifically, first of all, the reference direction calculation unit 722 specifies a pixel at which aliasing has occurred (to be referred to as an aliasing pixel hereinafter) among the respective edge directions in accordance with spatial continuity. The edge directions of the aliasing pixel and neighboring pixels are extremely discontinuous. The reference direction calculation unit 722 therefore determines that a pixel having an extremely discontinuous edge direction compared with the edge directions of the neighboring pixels is an aliasing pixel, and corrects the edge direction of the aliasing pixel based on the edge directions of the neighboring pixels. For example, the reference direction calculation unit 722 replaces the edge direction of the aliasing pixel with the edge direction of one of the neighboring pixels or a statistical value such as the average value of the neighboring edge directions. The reference direction calculation unit 722 then calculates a reference direction based on the edge direction of each pixel. In this manner, the reference direction calculation unit 722 can properly calculate a reference direction without any angle aliasing.

(Second Countermeasure): In the second countermeasure, the reference direction calculation unit 722 performs coordinate conversion of edge directions. More specifically, the reference direction calculation unit 722 converts the edge direction $\theta$ expressed by a radian into an edge direction x expressed by a two-dimensional unit vector in an angular coordinate system as indicated by equation (1).

$$\theta \Rightarrow x = (\cos\theta, \sin\theta) \quad (1)$$

The reference direction calculation unit 722 calculates a reference direction (average value) X represented by an orthogonal coordinate system based on a plurality (N) of edge directions $x_n$ as indicated by equation (2):

$$X = \frac{1}{N}\sum_{n=1}^{N} x_n = \left(\frac{1}{N}\sum_{n=1}^{N}\cos\theta_n, \frac{1}{N}\sum_{n=1}^{N}\sin\theta_n\right) = (X_1, X_2) \quad (2)$$

The reference direction calculation unit 722 then calculates a reference direction Θ expressed by each coordinate system from the reference direction X expressed by the orthogonal coordinate system as indicated by equation (3):

$$\Theta = \tan^{-1}\left(\frac{X_1}{X_2}\right) \quad (3)$$

In this manner, the reference direction calculation unit 722 can properly calculate a reference direction without angle aliasing. In the above description, a reference direction is an average value for the concrete execution of the second countermeasure. In the second countermeasure, however, a reference direction is not limited to an average value and may be any one of the following statistical values: a mode value, maximum value, minimum value, intermediate value, and the like.

The shift amount calculation unit 723 calculates the shift amount between the reference direction and each of edge directions calculated by the edge direction calculation unit 721. The shift amount calculation unit 723 calculates this shift amount as, for example, the inner product of two two-dimensional unit vectors in each edge direction and the reference direction.

The first calculation unit 724 counts, as an edge direction feature amount, the number of pixels included in a calculation target region in a contracted image, which have shift amounts smaller than the first threshold (to be referred to as the edge direction threshold hereinafter). It is preferable to perform threshold processing with the edge direction threshold in counting processing. For example, the first calculation unit 724 performs threshold processing for a contracted image with the edge direction threshold to generate a threshold image with a pixel value of "1" being assigned to each pixel having a brightness value smaller than the edge direction threshold and a pixel value of "0" being assigned to each pixel having a brightness value larger than the edge direction threshold. The first calculation unit 724 then counts, for example, the number of pixels included in the threshold image, which have a pixel value of "1". An edge direction threshold is determined according to an empirical rule. The edge direction threshold may be set to a value, for example, 0.5 or 0.6, that can discriminate between a statistically high average direction and a statistically low average edge direction based on, for example, the measurement results shown in FIG. 5. That is, an edge direction feature amount indicates the degree of how each of the pixels included in an ultrasonic image points in a specific direction. An edge direction feature amount is supplied to the filter characteristic selection unit 75, as shown in FIG. 6 or 11.

This is the end of the description of the first feature amount calculation unit 72. The reason why the shift amount of the edge direction of each pixel from the reference direction is calculated will be described below. Living tissues such as blood vessel walls and MSK run in the entire body in a complicated manner. When, for example, observing the blood vessel wall, as shown in FIG. 2, the edge directions in a calculation target region point in the horizontal direction from a global point of view. However, even in the blood vessel wall of the same diagnostic region, an edge direction in a calculation target region do not always point in the horizontal direction depending on the positions and the like of the blood vessels. For this reason, in order to measure the degree of how edges in the calculation target region point in the specific direction, it is preferable to calculate the shift amount of the edge direction of each pixel from the reference direction in the entire calculation target region. For these reasons, the first feature amount calculation unit 72 calculates the shift amount of the edge direction of each pixel from the reference direction. In other words, the first feature amount calculation unit 72 can detect that each edge direction in a calculation target region points in a specific direction, regardless of the position and the like of a living tissue.

In addition, setting a calculation target region in a local region of an ultrasonic image (or contracted image) instead of the entire ultrasonic image (or contracted image) can speed up the processing concerning edge direction feature amounts.

The second feature amount calculation unit 73, the filter characteristic storage unit 74, the filter characteristic selection unit 75, and the image filter unit 76 will be described by referring back to FIG. 6.

The second feature amount calculation unit 73 calculates the second feature amount (brightness feature amount) concerning a brightness value distribution in a calculation target region in an ultrasonic image. A brightness value distribution in a calculation target region indicates the tendency of brightness values distributed in the calculation target region in the ultrasonic image. A brightness value distribution in a calculation target region indicates a global brightness value distribution. Note that the image input to the second feature amount calculation unit 73 preferably has the same resolution as that of the image input to the first feature amount calculation unit 72. Therefore, the image contracting unit 71 also inputs a contracted image to the second feature amount calculation unit 73.

More specifically, the second feature amount calculation unit 73 counts, as a brightness feature amount, the number of pixels included in a calculation target region in a contracted image, which have shift amounts larger or smaller than the second threshold (to be referred to as the brightness threshold hereinafter). For example, the second feature amount calculation unit 73 performs threshold processing for the contracted image with a brightness threshold, and generates a threshold image with a pixel value of "1" being assigned to each pixel having a brightness value larger than the brightness threshold and a pixel value of "0" being assigned to each pixel having a brightness value smaller than the edge direction threshold. The second feature amount calculation unit 73 counts the number of pixels included in the threshold image, which have a pixel value of "1". A brightness threshold is determined according to an empirical rule. The brightness threshold may be set to a value, for example, 0.5, that can discriminate between a statistically high average brightness value and a statistically low average brightness value based on, for example, the measurement results shown in FIG. 5. In order to exclude a background region in a contracted image from pixel counting targets, threshold processing may be performed for a contracted image with a lower limit threshold for the removal of a background region other than a brightness threshold.

In addition, setting a calculation target region in a local region of an ultrasonic image (or a contracted image) instead of the entire ultrasonic image (or contracted image) can speed up the processing concerning brightness feature amounts.

The filter characteristic storage unit 74 stores the range of first feature amounts (edge direction feature amounts) and the range of second feature amounts (brightness feature amounts) which ultrasonic images can have and are suitable for each of filter characteristics in association with each filter characteristic. A filter characteristic is determined in accordance with a parameter set or an image filter type. For example, the filter characteristic storage unit 74 stores the range of edge direction feature amounts and the range of brightness feature amounts which ultrasonic images can have and are suitable for each of parameter sets respectively determining a filter characteristics in association with each parameter set.

FIG. 12 is a view showing an example of a table associating the range of first feature amounts (edge direction feature amounts and the range of second feature amounts (brightness feature amounts) with each of parameter sets. As shown in FIG. 12, both the range of edge direction feature amounts and the range of brightness feature amounts are associated with each parameter set on the table. For example, parameter set 1 is associated with both range 1-1 of edge direction feature mounts and range 2-1 of brightness feature amounts. Each parameter set is determined in advance for each diagnostic region or living tissue to allow proper filtering of ultrasonic images. Diagnostic regions and living tissues include, for example, the blood vessel, abdomen, muscle fiber, and heart. More specifically, the range of edge direction feature amounts and the range of brightness feature amounts are set according to an empirical rule concerning global edge directions and brightness value distributions which ultrasonic images including diagnostic regions and living tissue regions can have.

As an image filter according to this embodiment, a filter which executes at least one of sharpening, smoothing, noise reduction, and speckle reduction for an ultrasonic image is used. As an image filter according to this embodiment, there is available, for example, a linear sharpening filter, linear smoothing filter, or bilateral filter. In addition, as an image filter according to this embodiment, a nonlinear anisotropic diffusion filter which performs smoothing or sharpening dependently on edge directions may be used. The filter characteristics of an image filter such as a filter intensity and a filter direction are determined by parameter sets. Each parameter set includes kinds of parameters. Parameters according to this embodiment include, for example, a parameter indicating the degree of an increase or decrease in the brightness value of each pixel of an edge portion, a parameter indicating the degree of an increase or decrease in the brightness value of each pixel of a non-edge portion, a parameter indicating the direction of sharpening, a parameter indicating the degree of sharpening, a parameter indicating a smoothing direction, and a parameter indicating a smoothing intensity.

There is a region such as the breast with a cancer whose geometrical feature unique to an affected region is suppressed by being processed by an image filter. In this case, it is not proper to apply an image filter to an image. It therefore may be preferable to associate a code indicating inhibition of the application of an image filter (to be referred to as an image filter OFF code hereinafter) with the range of edge direction feature amounts and the range of brightness feature amounts which correspond to a diagnostic region or living tissue to which any image filter should not be applied.

The filter characteristic selection unit 75 selects a filter characteristic corresponding to both the edge direction feature amount calculated by the first feature amount calculation unit 72 and the brightness feature amount calculated by the second feature amount calculation unit 73 from the filter characteristics stored in the filter characteristic storage unit 74. More specifically, the filter characteristic selection unit 75 selects a filter characteristic associated with both a range including the edge direction feature amount calculated by the first feature amount calculation unit 72 and a range including the brightness feature amount calculated by the second feature amount calculation unit 73. The filter characteristic selection unit 75 can therefore select a filter characteristic suitable for a scanned diagnostic region or living tissue. A parameter set or image filter corresponding to the selected filter characteristic is supplied to the image filter unit 76. If an image filter type is fixed, the parameter set corresponding to the selected filter characteristic is selected. If no image filter type is fixed, the type of image filter corresponding to the selected filter characteristic is selected. The user can arbitrarily set, via an input device (not shown), selection targets of the filter characteristic selection unit 75. If an image filter OFF code is selected, the code is supplied to the image filter unit 76.

Upon receiving a parameter set from the filter characteristic selection unit 75, the image filter unit 76 applies an existing image filter having a filter characteristic corresponding to the supplied parameter set to an ultrasonic image. Upon receiving an image filter type from the filter characteristic selection unit 75, the image filter unit 76 applies the supplied type of image filter to an ultrasonic image. A filter target region to which the image filter is to be applied is limited to a kernel. The kernel has a predetermined size (kernel size). The kernel size is set to a size equal to or more than 3×3. The image filter unit 76 applies the image filter to pixels included in the kernel at each kernel position while sequentially changing the kernel position within the above range of the calculation target region. Applying this image filter can obtain a proper filtering effect in the diagnostic region or living tissue region depicted in the ultrasonic image. Note that upon receiving an image filter OFF code from the filter characteristic selection unit 75, the image filter unit 76 applies no image filter to the ultrasonic image. The display unit 90 displays the ultrasonic image from the image filter unit 76.

This is the end of the description of the image processing unit 70.

According to the above description, the image processing unit 70 includes the image contracting unit 71. However, the image processing unit 70 according to this embodiment is not limited to this, and may not include the image contracting unit 71. In this case, based on an original ultrasonic image from the image generation unit 60 or the storage unit 80, the first feature amount calculation unit 72 calculates an edge direction feature amount concerning the global edge direction of the original ultrasonic image. Likewise, based on an original ultrasonic image, the second feature amount calculation unit 73 calculates a brightness feature amount concerning the global brightness value distribution of the original ultrasonic image. Note that processing target pixels of the first feature amount calculation unit 72 and the second feature amount calculation unit 73 are limited to those in a calculation target region in an ultrasonic image. As described above, the matrix size of a calculation target region is larger than the kernel size of an image filter.

According to the above description, the ultrasonic diagnostic apparatus 1 includes the filter characteristic storage unit 74, the first feature amount calculation unit 72, the second feature amount calculation unit 73, the filter characteristic selection unit 75, and the image filter unit 76. The filter characteristic storage unit 74 stores the range of edge direction feature amounts and the range of brightness feature amounts which ultrasonic images can have and are suitable for each filter characteristic in association with each of filter characteristics. The first feature amount calculation unit 72 calculates an edge direction feature amount concerning an edge direction in a calculation target region in an ultrasonic image. The second feature amount calculation unit 73 calculates a brightness feature amount concerning a brightness value distribution in the calculation target region in the ultrasonic image. The filter characteristic selection unit 75 selects a filter characteristic corresponding to both the calculated edge direction feature amount and the calculated brightness feature amount from the filter characteristics stored in the filter characteristic storage unit 74. The image filter unit 76 applies an image filter having the selected filter characteristic to the ultrasonic image.

An ultrasonic image has an edge direction and brightness value distribution unique to each diagnostic region or living tissue. Therefore, the filter characteristic selection unit 75 can select a filter characteristic suitable for a diagnostic region or living tissue as a scan target. The image filter unit 76 can apply an image filter having a filter characteristic suitable for the diagnostic region or living tissue as the scan target to the ultrasonic image. Even if, therefore, the ultrasonic probe 10 is moved during ultrasonic examination and the diagnostic region or living tissue as the scan target before the movement differs from that after the movement, it is possible to apply an image filter suitable for the diagnostic region or living tissue as the scan target to the ultrasonic image. Displaying the ultrasonic image after filtering allows the operator to properly observe a lesion or the like.

It is preferable to obtain the same filtering effect in different diagnostic regions in an ultrasonic image concerning a living tissue distributed in a wide region in a human body such as the blood vessels or MSK. Conventionally, however, since parameter sets for filter characteristics are preset in accordance with diagnostic regions, it is not possible to obtain the same filtering effect.

The ultrasonic diagnostic apparatus 1 according to this embodiment can, however, apply an image filter suitable for a living tissue as a scan target to an ultrasonic image, and hence can obtain a constant filtering effect even in an ultrasonic image concerning a living tissue distributed in a wide region in the human body such as the blood vessels regardless of diagnostic regions.

This embodiment can therefore provide the ultrasonic diagnostic apparatus 1 and the medical image processing apparatus 100 which can improve image diagnostic performance.

Example 1

The following is Example 1 of this embodiment which uses multi-resolution analysis for image contraction processing and uses a nonlinear anisotropic diffusion filter as an image filter. Assume that Example 1 is configured to select a proper parameter set from parameter sets concerning a nonlinear anisotropic diffusion filter. Note that this embodiment is provided with the image contraction unit and the image filter unit as separate units. However, an ultrasonic diagnostic apparatus according to Example 1 is not limited to this. The ultrasonic diagnostic apparatus according to Example 1 has image contraction processing incorporated in an algorithm for an image filter. Note that the same reference numerals denote constituent elements having almost the same functions as those in this embodiment in the following description, and a repetitive description will be made only when required.

FIG. 13 is a block diagram showing the arrangement of an image processing unit 110 according Example 1. As shown in FIG. 13, the image processing unit 110 has a multilayer structure constituted by levels to perform multi-resolution analysis/synthesis. Referring to FIG. 13, for the sake of a concrete description, assume that the highest level of multi-resolution analysis/synthesis is 3. However, this embodiment need not be limited to this. Multi-resolution analysis/synthesis may be performed within the range of level 1 to level n (n is a natural number equal to or more than 2). Example 1 uses discrete wavelet transform/inverse transform as an example of multi-resolution analysis/synthesis. However, Example 1 need not be limited to this. For example, it is possible to use a Laplacian pyramid method or Gabor transform/inverse transform as multi-resolution analysis/synthesis.

As shown in FIG. 13, the image processing unit 110 includes, for the respective levels, multi-resolution analysis units 111, i.e., 111-1, 111-2, and 111-3, low pass image filter units 113, i.e., 113-1, 113-2, and 113-3, high pass image filter units 115, i.e., 115-1, 115-2, and 115-3, and multi-resolution synthesis units 117, i.e., 117-1, 117-2, and 117-3.

The multi-resolution analysis unit 111 generates a low-frequency image and a high-frequency image which have resolutions lower than that of a processing target image, based on the processing target image. For example, the multi-resolution analysis unit 111 performs, for example, discrete wavelet transform for the processing target image. In discrete wavelet transform, the multi-resolution analysis unit 111 applies a one-dimensional low pass filter and a one-dimensional high pass filter in each axis direction (each dimension) of an x-y orthogonal coordinate system. Applying these filters will decompose the processing target image into one low-frequency image and three high-frequency images. The low-frequency image includes low-frequency components of the spatial frequency components of the processing target image. Each high-frequency image includes high-frequency components, of the spatial frequency components of the processing target image, which are located in at last one direction. The number of samples per coordinate axis of each image after the multi-resolution analysis is contracted to ½ the number of samples per each coordinate axis before the multi-resolution analysis.

If the multi-resolution analysis unit 111 belongs to the lowest level (level 1 in the case of FIG. 13), a processing target image is an original ultrasonic image from an image generation unit 60 or a storage unit 80. If the multi-resolution analysis unit 111 does not belong to the lowest level (level 1 in the case of FIG. 13), a processing target image is a low-frequency image from the multi-resolution analysis unit 111 at the immediately lower level.

If the multi-resolution analysis unit 111 belongs to the highest level (level 3 in the case of FIG. 13), a generated low-frequency image is supplied to the low pass image filter unit 113-3 at the same highest level. If the multi-resolution analysis unit 111 does not belong to the highest level, a generated low-frequency image is supplied to the multi-resolution analysis unit 111 belonging to the immediately lower level. The three generated high-frequency images are supplied to the high pass image filter unit 115 belonging to the same level.

The low pass image filter unit 113 selects a parameter set that produces a filtering effect optimal for a processing target image by using an edge direction and brightness value distribution unique to each diagnostic region or living tissue based on the global edge direction and brightness value distribution which the processing target image has, and applies a nonlinear anisotropic diffusion filter having a filter characteristic corresponding to the selected parameter set to the processing target image. A nonlinear anisotropic diffusion filter is an image filter which smoothes information in a direction tangential to an edge and sharpens information in a direction normal to the edge. The image processed by the nonlinear anisotropic diffusion filter is supplied to the multi-resolution synthesis unit 117 at the same level.

If the low pass image filter unit 113 belongs to the highest level (level 3 in the case of FIG. 13), a processing target image is a low-frequency image from the multi-resolution analysis unit 111 belonging to the same highest level. If the low pass image filter unit 113 does not belong to the highest level, a processing target image is an image from the multi-resolution synthesis unit 117 belonging to the immediately higher level.

FIG. 14 is a block diagram showing the arrangement of the low pass image filter unit 113. As shown in FIG. 14, the low pass image filter unit 113 includes a first feature amount calculation unit 72, a second feature amount calculation unit 73, a filter characteristic storage unit 74, a filter characteristic selection unit 75, and an image filter unit 76.

The first feature amount calculation unit 72 calculates an edge direction and edge intensity for each of the pixels included in a processing target image. The first feature amount calculation unit 72 calculates an edge direction feature amount concerning the global edge direction of an ultrasonic image. A combination of an edge intensity and an edge direction is called edge information. An edge direction feature amount is calculated only within a calculation target region.

The second feature amount calculation unit 73 calculates a brightness feature amount concerning the global brightness value distribution of an ultrasonic image. A brightness feature amount is calculated only within a calculation target region.

The filter characteristic storage unit 74 stores the range of edge direction feature amounts and the range of brightness feature amounts which an ultrasonic image can have and are suitable for each filter characteristic in association with each of parameter sets that respectively determine filter characteristics. Each parameter set includes parameters that determine the filter characteristic of a nonlinear anisotropic diffusion filter. These parameters include, for example, a smoothing intensity, sharpening intensity, and edge detection sensitivity. A parameter set may be set for each level or may not be set for each level.

The filter characteristic selection unit 75 selects a parameter set corresponding to both the edge direction feature amount calculated by the first feature amount calculation unit 72 and the brightness feature amount calculated by the second feature amount calculation unit 73 from the parameter sets stored in the filter characteristic storage unit 74.

The image filter unit 76 applies a nonlinear anisotropic diffusion filter having a filter characteristic corresponding to a parameter set from the filter characteristic selection unit 75 to an ultrasonic image. The image filter unit 76 uses a nonlinear anisotropic diffusion filter having a kernel size equal to or more than a size of 3×3. The image filter unit 76 applies a nonlinear anisotropic diffusion filter at each kernel position while sequentially changing the kernel of the nonlinear anisotropic diffusion filter within the range of the above calculation target region. Applying this image filter can obtain a proper filtering effect in the diagnostic region or living tissue region depicted in the ultrasonic image.

This is the end of the description of the low pass image filter unit 113.

The high pass image filter unit 115 and the multi-resolution synthesis unit 117 will be described by referring back to FIG. 13.

The high pass image filter unit 115 controls the brightness value of each of three high-frequency images from the multi-resolution analysis unit 111 by using edge information from the low pass image filter unit 113. More specifically, the high pass image filter unit 115 multiplies each of pixels included in each high-frequency image by a parameter corresponding to edge information. This parameter includes the first parameter for an edge region and the second parameter for a non-edge region. The first parameter is set to enhance the edge region. The second parameter is set to suppress the non-edge region. The high-frequency image whose brightness value is controlled by the high pass image filter unit 115 is supplied to the multi-resolution synthesis unit 117. Note that in the high pass image filter unit 115, a nonlinear anisotropic diffusion filter like the low pass image filter unit 113 may be applied to a high-frequency image.

The multi-resolution synthesis unit 117 generates an output image having a resolution higher than that of a low-frequency image and a high-frequency image based on a low-frequency image from the low pass image filter unit 113 and three high-frequency images from the high pass image filter unit 115. More specifically, the multi-resolution synthesis unit 117 performs multi-resolution synthesis such as discrete wavelet inverse transform for the low-frequency image and the three high-frequency images. The number of samples per coordinate axis of the output image after the multi-resolution synthesis is increased to two times the number of samples per each coordinate axis before multi-resolution synthesis.

If the multi-resolution synthesis unit 117 does not belong to the lowest level (level 1 in the case of FIG. 13), the output image is supplied to the low pass image filter unit 113 belonging to the immediately lower level. If the multi-resolution synthesis unit 117 belongs to the lowest level, the output image is supplied from the image processing unit 110 to a display unit 90 to be displayed.

This is the end of the description of the image processing unit 110 according to Example 1.

As described above, the ultrasonic diagnostic apparatus according to Example 1 includes the multi-resolution analysis units 111, the first feature amount calculation unit 72, the second feature amount calculation unit 73, the filter characteristic storage unit 74, the filter characteristic selection unit 75, and the image filter unit 76. The multi-resolution analysis unit 111 performs multi-resolution analysis for an ultrasonic image to generate a low-frequency image and a high-frequency image on spatial frequencies at each of resolution levels. The first feature amount calculation unit 72 calculates the first feature amount in the global edge direction of a low-frequency image. The second feature amount calculation unit 73 calculates the second feature amount concerning the global edge intensity distribution and brightness value distribution of the low-frequency image. The filter characteristic storage unit 74 stores the range of first feature amounts and the range of second feature amounts which an ultrasonic image can have and are suitable for each of filter characteristics in association with each filter characteristic. The filter characteristic selection unit 75 selects a filter characteristic corresponding to both the first feature amount calculated by the first feature amount calculation unit 72 and the second feature amount calculated by the second feature amount calculation unit 73 from filter characteristics. The image filter unit 76 applies an image filter having the selected filter characteristic to at least one of the low-frequency image and the high-frequency image.

In Example 1, filtering is performed at each level upon multi-resolution analysis. This can therefore improve the image quality of the ultrasonic image as compared with a case in which filtering is performed after multi-resolution synthesis at level 1.

Example 1 can therefore provide an ultrasonic diagnostic apparatus and an ultrasonic image processing apparatus which can improve image diagnostic performance.

Note that it is possible to use both a brightness feature amount and an edge intensity feature amount. In addition, after the number of dimensions is increased by spatially dividing an image into sub-regions and obtaining a feature amount for each sub-region, the number of dimensions may be decreased by using a technique such as principal component analysis.

The filter characteristic selection unit 75 may use a statistical algorithm such as a Fisher linear discriminant function or AbaBoost Algorithm for the selection of a parameter set. For example, it is preferable to use the edge direction feature amounts and brightness feature amounts of ultrasonic images of known diagnostic regions and living tissues as learning sample data for these statistical algorithms.

(Modification)

The second feature amount calculation unit 73 according to this embodiment calculates a brightness feature amount concerning a global brightness value distribution as the second feature amount. However, the second feature amount calculation unit 73 according to the embodiment is not limited to this, and may calculate an edge intensity feature amount concerning a global edge intensity distribution as the second feature amount. The image processing unit 70 according to this modification will be described in detail below. Note that the same reference numerals denote constituent elements having almost the same functions as those in this embodiment in the following description, and a repetitive description will be made only when required.

FIG. 15 is a block diagram showing the arrangement of the second feature amount calculation unit according to the modification of this embodiment. As shown in FIG. 15, the second feature amount calculation unit includes an edge intensity calculation unit 732 and a second counting unit 733. A processing target of the second feature amount calculation unit according to the modification may be either an original ultrasonic image or a contracted image of the original ultrasonic image. However, for the same of a concrete description given below, a processing target of the second feature amount calculation unit according to the modification is a contracted image.

The edge intensity calculation unit 732 calculates the edge intensity of each of the pixels included in a calculation target region in a contracted image based on the spatial derivative of the brightness values of the pixels. More specifically, first of all, the edge intensity calculation unit 732 calculates a spatial derivative by spatial differentiation along each coordinate axis of an ultrasonic image by using a processing target pixel and neighboring pixels of the processing target pixel like the edge direction calculation unit 721, thereby calculating a spatial derivative. The edge intensity calculation unit 732 then calculates an edge intensity concerning the processing target pixel based on the calculated spatial derivative.

The second counting unit 733 counts, as an edge intensity feature amount, the number of pixels included in a calculation target region in a contracted image, which have edge intensities lower than the third threshold (to be referred to as an edge intensity threshold hereinafter). In counting processing, it is preferable to perform threshold processing using an edge intensity threshold. That is, the second counting unit 733 performs threshold processing for a contracted image by using an edge intensity threshold to generate a threshold image with a pixel value of "1" being assigned to each pixel having an edge intensity lower than the edge intensity threshold and a pixel value of "0" being assigned to each pixel having an edge intensity larger than the edge threshold. The second counting unit 733 counts the number of pixels included in the threshold image, which have a pixel value of "1". The second counting unit 733 determines an edge intensity threshold according to an empirical rule.

This is the end of the description of the second feature amount calculation unit according to the modification.

Note that the filter feature storage unit according to this modification stores the range of edge direction feature amounts and the range of edge intensity feature amounts which ultrasonic images can have and are suitable for each of filter characteristics in association with each filter characteristic. The filter characteristic selection unit according to the first modification selects a filter characteristic corresponding to both the edge direction feature amount calculated by the first feature amount calculation unit 72 and the edge intensity feature amount calculated by the second feature amount calculation unit from the filter characteristics stored in the filter characteristic storage unit according to the modification. The image filter unit according to the first modification applies an image filter having the filter characteristic from the filter characteristic selection unit to the ultrasonic image.

This modification can therefore provide an ultrasonic diagnostic apparatus, medical image processing apparatus, and medical image processing method which can improve image diagnostic performance.

Example 2

Example 1 described above is configured to select a parameter set corresponding to an edge direction feature amount and a brightness feature amount or an edge intensity feature amount from parameter sets of a single image filter (more specifically, a nonlinear anisotropic diffusion filter). However, this embodiment is not limited to this. An ultrasonic diagnostic apparatus 1 according to Example 2 selects an image filter corresponding to an edge direction feature amount and a brightness feature amount or an edge intensity feature amount from image filters, as described above. An ultrasonic diagnostic apparatus, medical image processing apparatus, and medical image processing method according to Example 2 will be described below.

FIG. 16 is a block diagram showing the arrangement of an image processing unit 120 according to Example 2. As shown in FIG. 16, the image processing unit 120 includes an image contracting unit 71, a first feature amount calculation unit 72, a second feature amount calculation unit 73, a filter selection unit 81, an image filter unit 82, and a switching unit 83.

The image filter unit 82 is configured to selectively apply image filters respectively having filter characteristics. Image filters that can be applied include linear filters (a Gaussian filter, differential filter, wavelet filter, and the like) and nonlinear filters (a median filter, morphological filter, non-local means filter, and bi-lateral filter), anisotropic diffusion filters (an anisotropic diffusion filter and the like), and combinations of them. In addition, options for selecting mage filters may include an option for not using any image filter (that is, an option for only passing all signals). The number of image filters to be used may be any number equal to or more than 2. For the sake of a concrete description, assume that two image filters including a first image filter 82-1 and a second image filter 82-2 are used.

The filter section unit 81 selects a specific image filter from a image filters in the image filter unit to apply an image filter having a filter characteristic corresponding to both the edge direction feature amount calculated by the first feature amount calculation unit 72 and the brightness feature amount or edge intensity feature amount calculated by the second feature amount calculation unit 73 to an ultrasonic image as a processing target. The selected image filter is activated while the image filter which has not been selected is stopped. The identifier of the selected image filter is supplied to the switching unit 83.

The switching unit 83 switchably connects between output terminals P1 of image filters and an output terminal P2 of the image processing unit 120. The switching unit 83 connects the output terminal P1 of an image filter corresponding to an identifier from the filter selection unit 81 to the output terminal P2. This makes the image processing unit 120 output an output image from the image filter selected by the filter selection unit 81.

As described above, the second modification is configured to select an image filter having a filter characteristic corresponding to an edge direction feature and a brightness feature amount or an edge intensity feature amount from image filters.

The second modification can therefore provide an ultrasonic diagnostic apparatus, medical image processing apparatus, and medical image processing method which can improve image diagnostic performance.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
an ultrasonic probe configured to transmit an ultrasonic wave to a subject, receive the ultrasonic wave reflected by the subject, and generate an echo signal corresponding to the received ultrasonic wave;
a processor is configured to:
generate an ultrasonic image concerning the subject based on the echo signal, wherein the ultrasonic image comprises a plurality of pixels,
calculate a plurality of elements of a structure tensor for each pixel in a specific region of the ultrasonic image by a spatial derivative of using a brightness value of each pixel in the specific region, the specific region being larger than a kernel size of a filter to be applied to the ultrasonic images,
calculate an eigenvalue of the structure tensor by a linear algebraic computation of the plurality of elements of the structure tensor to obtain an edge direction for each pixel in the specific region of the ultrasonic image based on the eigenvalue of the structure tensor,
calculate a shift amount of each pixel in the specific region by comparing the edge direction with a reference edge direction,
compare the shift amount of each pixel in the specific region to a first threshold and count a first number of pixels having the respective shift amount smaller than the first threshold in the each pixel in the specific region,
compare the brightness value of each pixel in the specific region to a second threshold or an edge intensity of each pixel in the specific region to a third threshold and count a second number of pixels having the respective brightness value larger than the second threshold or having the respective edge intensity larger than the third threshold, in each pixel in the specific region, the respective edge intensity calculated by the spatial derivative of the respective brightness value of each pixel in the specific region,
store a plurality of filters having a plurality of respective characteristics different from each other,
select a filter from among the plurality of filters, the filter having a set of filter characteristics, from among the plurality of filters, corresponding to both of the first number of the pixels and the number of the second number of the pixels, and
generate a display image by applying the filter having the set of selected filter characteristics to the ultrasonic images; and
a display configured to display the display image.

2. The apparatus of claim 1, wherein the specific region is a partial region smaller than a matrix size of the ultrasonic image.

3. The apparatus of claim 1, wherein the specific region is set in accordance with an instruction from a user.

4. The apparatus of claim 1, wherein a plurality of the specific regions are set in the ultrasonic image, and
the processor is further configured to, for each of the specific regions, count the first number of pixels, count the second number of pixels, select the filter from the plurality of filters, and apply the filter to the specific region.

5. The apparatus of claim 1, wherein the processor is further configured to segment the ultrasonic image into a plurality of regions, and set the specific region in each of the segmented regions, and
the processor is further configured to, for each of the specific regions, count the first number of pixels, count the second number of pixels, select the filter from the plurality of filters, and apply the filter to the specific region.

6. The apparatus of claim 1, wherein the processor is further configured to segment the ultrasonic image into a plurality of regions in accordance with a depth direction, and
the processor is further configured to, for each of the specific regions, count the first number of pixels, count the second number of pixels, select the filter from the plurality of filters, and apply the filter to the specific region.

7. The apparatus of claim 1, wherein the processor is further configured to extract an anatomical region by segmentation processing and set the specific region in the extracted anatomical region.

8. A medical image processing apparatus comprising:
a first storage unit configured to store an ultrasonic image concerning a subject, wherein the ultrasonic image comprises a plurality of pixels;
a processor configured to:
calculate a plurality of elements of a structure tensor for each pixel in a specific region of the ultrasonic image by a spatial derivative of a brightness value of each pixel in the specific region, the specific region being larger than a kernel size of a filter to be applied to the ultrasonic images,
calculate an eigenvalue of the structure tensor by a linear algebraic computation of the plurality of elements of the structure tensor to obtain an edge direction for each pixel in the specific region of the ultrasonic image based on the eigenvalue of the structure tensor,
calculate a shift amount of each pixel in the specific region by comparing the edge direction with a reference edge direction,
compare the shift amount of each pixel in the specific region to a first threshold and count a first number of pixels having the respective shift amount smaller than the first threshold in each pixel in the specific region,
compare the brightness value of each pixel in the specific region to a second threshold or an edge intensity of each pixel in the specific region to a third threshold and count a second number of pixels having the respective brightness value larger than the second threshold or having the respective edge intensity larger than the third threshold, in each pixel in the specific region, the respective edge intensity calculated by the spatial derivative of the respective brightness value of each pixel in the specific region,
store a plurality of filters having a plurality of filter characteristics different from each other,
select a filter from among the plurality of filters, the filter having a set of filter characteristics, corresponding to both of the first number of the pixels and the second number of the pixels, and
generate a display image by applying the filter having the set of selected filter characteristics to the ultrasonic images; and
a display configured to display the display image.

9. An ultrasonic diagnostic apparatus comprising:
an ultrasonic probe configured to transmit an ultrasonic wave to a subject, receive the ultrasonic wave reflected by the subject, and generate an echo signal corresponding to the received ultrasonic wave; and
a processor configured to:
generate an ultrasonic image concerning the subject based on the echo signal, calculate a plurality of elements of a structure tensor for each pixel in a specific region of the ultrasonic image by a spatial derivative of a brightness value of each pixel in the specific region, the specific region being larger than a kernel size of a filter to be applied to the ultrasonic image, wherein the ultrasonic image comprises a plurality of pixels,
calculate an eigenvalue of the structure tensor by a linear algebraic computation of the plurality of elements of the structure tensor to obtain an edge direction for the each pixel in the specific region of the ultrasonic image based on the eigenvalue of the structure tensor,
calculate a shift amount of each pixel in the specific region by comparing the edge direction with a reference edge direction,
compare the shift amount of each pixel in the specific region to a first threshold and count a first number of pixels having the respective shift amount larger than the first threshold in each pixel in the specific region,
compare the brightness value of each pixel in the specific region to a second threshold or an edge intensity of each pixel in the specific region to a third threshold and count a second number of pixels having the respective brightness value larger than the second threshold or having the respective edge intensity larger than the third threshold, in each pixel in the specific region, the respective edge intensity calculated by the spatial derivative of the respective brightness value of each pixel in the specific region,
store a plurality of filters having a plurality of respective filter characteristics different from each other,
select a filter from among the plurality of filters, the filter having a set of filter characteristics, corresponding to both of the first number of the pixels and the second number of the pixels, and
generate a display image by applying the filter having the set of selected filter characteristics to the ultrasonic image, and
a display configured to display the display image.

10. An ultrasonic diagnostic apparatus comprising:
an ultrasonic probe configured to transmit an ultrasonic wave to a subject, receive the ultrasonic wave reflected by the subject, and generate an echo signal corresponding to the received ultrasonic wave; and
a processor configured to:
generate an ultrasonic image concerning the subject based on the echo signal, calculate a plurality of elements of a structure tensor for each pixel in a specific region of the ultrasonic image by a spatial derivative of a brightness value of each pixel in the specific region, the specific region being larger than a kernel size of a filter to be applied to the ultrasonic image, wherein the ultrasonic image comprises a plurality of pixels,
calculate an eigenvalue of the structure tensor by a linear algebraic computation of the plurality of elements of the structure tensor to obtain an edge direction for the each pixel in the specific region of the ultrasonic image based on the eigenvalue of the structure tensor,
calculate a shift amount of each pixel in the specific region by comparing the edge direction with a reference edge direction,
compare the shift amount of each pixel in the specific region to a first threshold and count a first number of pixels having the respective shift amount smaller than the first threshold in each pixel in the specific region,
compare the brightness value of each pixel in the specific region to a second threshold or an edge intensity of each pixel in the specific region to a third threshold and count a second number of pixels having the respective brightness value smaller than the second threshold or having the respective edge intensity smaller than the third threshold, in each pixel in the specific region, the respective edge intensity calculated by the spatial derivative of the respective brightness value of each pixel in the specific region, store a plurality of filters having a plurality of respective filter characteristics different from each other, select a filter from among the plurality of filters, the filter having a set of filter characteristics, corresponding to both of the first number of the pixels and the second number of the pixels, and generate a display image by applying the filter having the set of selected filter characteristics to the ultrasonic image; and a display configured to display the display image.

11. An ultrasonic diagnostic apparatus comprising:

an ultrasonic probe configured to transmit an ultrasonic wave to a subject, receive the ultrasonic wave reflected by the subject, and generate an echo signal corresponding to the received ultrasonic wave; and a processor configured to:

generate an ultrasonic image concerning the subject based on the echo signal, calculate a plurality of elements of a structure tensor for each pixel in a specific region of the ultrasonic image by a spatial derivative of a brightness value of each pixel in the specific region, the specific region being larger than a kernel size of a filter to be applied to the ultrasonic image, wherein the ultrasonic image comprises a plurality of pixels, calculate an eigenvalue of the structure tensor by a linear algebraic computation of the plurality of elements of the structure tensor to obtain an edge direction for each pixel in the specific region of the ultrasonic image based on the eigenvalue of the structure tensor, calculate a shift amount of each pixel in the specific region by comparing the edge direction with a reference edge direction, compare the shift amount of each pixel in the specific region to a first threshold and count a first number of pixels having the respective shift amount larger than the first threshold in each pixel in the specific region, compare the brightness value of each pixel in the specific region to a second threshold or an edge intensity of each pixel in the specific region to a third threshold and count a second number of pixels having the respective brightness value smaller than the second threshold or having the respective edge intensity smaller than the third threshold, in each pixel in the specific region, the respective edge intensity calculated by the spatial derivative of the respective brightness value of each pixel in the specific region, store a plurality of filters having a plurality of respective filter characteristics different from each other, select a filter from among the plurality of filters, the filter having a set of filter characteristics, corresponding to both of the first number of the pixels and the second number of the pixels, and generate a display image by applying the filter having the set of selected filter characteristics to the ultrasonic image; and a display configured to display the display image.

* * * * *